(12) United States Patent
Heidecke et al.

(10) Patent No.: US 10,261,087 B2
(45) Date of Patent: Apr. 16, 2019

(54) DIAGNOSIS OF CANCER BY DETECTING AUTO-ANTIBODIES AGAINST VASCULAR ENDOTHELIAL GROWTH FACTOR (VEGF)

(71) Applicant: CELLTREND GMBH, Luckenwalde (DE)

(72) Inventors: Harald Heidecke, Berlin (DE); Kai Schulze-Forster, Berlin (DE)

(73) Assignee: CELLTREND GMBH, Luckenwal (DE)

( * ) Notice: Subject to any disclaimer, the term of this patent is extended or adjusted under 35 U.S.C. 154(b) by 0 days.

(21) Appl. No.: 15/115,902

(22) PCT Filed: Feb. 3, 2015

(86) PCT No.: PCT/EP2015/052184
§ 371 (c)(1),
(2) Date: Aug. 1, 2016

(87) PCT Pub. No.: WO2015/117953
PCT Pub. Date: Aug. 13, 2015

(65) Prior Publication Data
US 2017/0254812 A1 Sep. 7, 2017
US 2018/0267047 A2 Sep. 20, 2018

(30) Foreign Application Priority Data
Feb. 4, 2014 (EP) .................................. 14153823

(51) Int. Cl.
| | |
|---|---|
| *G01N 33/564* | (2006.01) |
| *G01N 33/574* | (2006.01) |
| *C07K 16/22* | (2006.01) |
| *G01N 33/74* | (2006.01) |
| *C07K 14/515* | (2006.01) |
| *C07K 16/28* | (2006.01) |
| *C07K 16/30* | (2006.01) |
| *G16H 50/30* | (2018.01) |
| *G16H 50/20* | (2018.01) |
| *G16H 10/40* | (2018.01) |

(52) U.S. Cl.
CPC ..... *G01N 33/57449* (2013.01); *C07K 14/515* (2013.01); *C07K 16/2863* (2013.01); *C07K 16/30* (2013.01); *C07K 16/3069* (2013.01); *G01N 33/564* (2013.01); *G01N 33/74* (2013.01); *C07K 2317/24* (2013.01); *C07K 2317/76* (2013.01); *G01N 2333/475* (2013.01); *G01N 2800/52* (2013.01); *G01N 2800/56* (2013.01); *G16H 10/40* (2018.01); *G16H 50/20* (2018.01); *G16H 50/30* (2018.01)

(58) Field of Classification Search
None
See application file for complete search history.

(56) References Cited

FOREIGN PATENT DOCUMENTS
| WO | 2005/016126 A2 | 2/2005 |
| WO | 2005/043165 A2 | 5/2005 |
| WO | 2007/071947 A1 | 6/2007 |

OTHER PUBLICATIONS

Park et al., Korean J Radiol 5(1):11-18, Mar. 2004.*
Wei Y-Q et al "Immunogene therapy of tumors with vaccine based on Xenopus homologous vascular endothelial growth factor as a model antigen", Proceedings of the National Academy of Sciences, National Academy of Sciences, vol. 98, No. 20, (Sep. 25, 2001), pp. 11545-11550, XP002248645.
International Search Report of PCT/EP2015/052184 dated Apr. 14, 2015.

* cited by examiner

*Primary Examiner* — Marianne P Allen
(74) *Attorney, Agent, or Firm* — McBee Moore Woodward & Vanik IP, LLC; Susan McBee; Chester Moore

(57) ABSTRACT

The present invention relates to a method for diagnosis of a cancer, comprising the steps of (i) determining the level of antibodies against vascular endothelial growth factor (VEGF) in a sample from a subject to be diagnosed, (ii) comparing the determined level in the sample to a control level derived from subjects without cancer; wherein a decreased level in the sample from the subject to be diagnosed as compared to the control level is indicative for cancer in the subject. Furthermore, the invention relates to method of predicting response and outcome of a treatment of a cancer with an angiogenesis inhibitor.

3 Claims, 12 Drawing Sheets
Specification includes a Sequence Listing.

A

B

C

DIAGNOSIS OF CANCER BY DETECTING AUTO-ANTIBODIES AGAINST VASCULAR ENDOTHELIAL GROWTH FACTOR (VEGF)

CROSS REFERENCE TO RELATED APPLICATIONS

This application is a § 371 National State Application of PCT/EP2015/052184, filed Feb. 3, 2015, which claims priority to European Application No. 14153823.1 filed Feb. 4, 2014.

BACKGROUND

Field of the Invention

The present invention is in the field of diagnostics, prognosis and therapeutics for cancer, more in particular in the field of diagnosis and therapy of VEGF or VEGFR associated cancer, more particular in the field of diagnosis, prognosis and therapy of ovarian cancer.

Background of the Invention

According to the American Cancer Society ovarian cancer is expected to account for over 22,000 new cancer diagnoses and more than 14,000 deaths in 2013 in the US alone. Of the gynaecologic malignancies, ovarian cancer has the highest mortality rate. In early stages of the disease, ovarian cancer is nearly asymptomatic. Hence, a large portion of the patients present with clinically advanced stages of ovarian cancer. However, the 5-year survival rate for patients diagnosed with early-stage disease is often >90%, but it is <20% for advanced-stage disease, underscoring the importance of early detection.

Current diagnosis of ovarian cancer relies on pelvic exam, transvaginal ultrasonography, (TVS), abdominal ultrasonography, and exploratory or diagnostic laparoscopy. The most commonly used biomarker for clinical screening and prognosis in patients with ovarian cancer is ovarian cancer antigen 125 (CA125) (Coticchia et al. (2008), J. Natl. Compr. Canc. Netw. 6(8):795-802). Serum CA125 levels are elevated in ≈80% of patients with advanced-stage epithelial ovarian cancer but are increased in only 50-60% of patients with early-stage disease. Serum CA125 levels may be falsely elevated in women with any i.p. pathology resulting in irritation of the serosa of the peritoneum or pericardium, uterine fibroids, renal disorders, and normal menses. Moreover, serum CA125 levels do not predict the outcome of cytoreductive surgery in patients with advanced epithelial ovarian cancer. Further biomarkers include, for example, Human Epidymis Protein 4 (HE4) and Mesothelin (Sarojini et al. (2012), Journal of Oncology 102, Article ID 709049). Severeness of ovarian cancer is categorized by the grade and stage of tumorization. This nowadays can only be performed by evaluation of the tumors under or after surgical treatment or by combining marker evaluation and (histological) evaluation of tissue. Staging is very important because ovarian cancers have different prognosis at different stages and may be treated differently. The accuracy of the staging may determine whether or not a patient will be cured. If the cancer isn't accurately staged, then cancer that has spread outside the ovary might be missed and not treated. Once a stage has been given it does not change, even when the cancer comes back or spreads to new locations in the body.

Ovarian cancer staging is by FIGO staging system uses information obtained after surgery, which can include a total abdominal hysterectomy, removal of (usually) both ovaries and fallopian tubes, (usually) the omentum, and pelvic (peritoneal) washings for cytopathology. The AJCC stage is the same as the FIGO stage. The AJCC staging system describes the extent of the primary Tumor (T), the absence or presence of metastasis to nearby lymph Nodes (N), and the absence or presence of distant Metastasis (M).

Stage I Limited to One or Both Ovaries
    IA involves one ovary; capsule intact; no tumor on ovarian surface; no malignant cells in ascites or peritoneal washings
    IB involves both ovaries; capsule intact; no tumor on ovarian surface; negative washings
    IC tumor limited to ovaries with any of the following: capsule ruptured, tumor on ovarian surface, positive washings Stage II Pelvic Extension or Implants
    IIA extension or implants onto uterus or fallopian tube; negative washings
    IIB extension or implants onto other pelvic structures; negative washings
    IIC pelvic extension or implants with positive peritoneal washings Stage III Peritoneal Implants Outside of the Pelvis; or Limited to the Pelvis with Extension to the Small Bowel or Omentum
    IIIA microscopic peritoneal metastases beyond pelvis
    IIIB macroscopic peritoneal metastases beyond pelvis less than 2 cm in size
    IIIC peritoneal metastases beyond pelvis >2 cm or lymph node metastases Stage IV Distant Metastases to the Liver or Outside the Peritoneal Cavity Para-aortic lymph node metastases are considered regional lymph nodes (Stage IIIC). As there is only one para-aortic lymph node intervening before the thoracic duct on the right side of the body, the ovarian cancer can rapidly spread to distant sites such as the lung.

The AJCC/TNM staging system includes three categories for ovarian cancer, T, N and M. The T category contains three other subcategories, T1, T2 and T3, each of them being classified according to the place where the tumor has developed (in one or both ovaries, inside or outside the ovary). The T1 category of ovarian cancer describes ovarian tumors that are confined to the ovaries, and which may affect one or both of them. The sub-subcategory T1a is used to stage cancer that is found in only one ovary, which has left the capsule intact and which cannot be found in the fluid taken from the pelvis. Cancer that has not affected the capsule, is confined to the inside of the ovaries and cannot be found in the fluid taken from the pelvis but has affected both ovaries is staged as T1b. T1c category describes a type of tumor that can affect one or both ovaries, and which has grown through the capsule of an ovary or it is present in the fluid taken from the pelvis. T2 is a more advanced stage of cancer. In this case, the tumor has grown in one or both ovaries and is spread to the uterus, fallopian tubes or other pelvic tissues. Stage T2a is used to describe a cancerous tumor that has spread to the uterus or the fallopian tubes (or both) but which is not present in the fluid taken from the pelvis. Stages T2b and T2c indicate cancer that metastasized to other pelvic tissues than the uterus and fallopian tubes and which cannot be seen in the fluid taken from the pelvis, respectively tumors that spread to any of the pelvic tissues (including uterus and fallopian tubes) but which can also be found in the fluid taken from the pelvis. T3 is the stage used to describe cancer that has spread to the peritoneum. This stage provides information on the size of the metastatic tumors (tumors that are located in other areas of the body, but are caused by ovarian cancer). These tumors can be very small, visible only under the microscope (T3a), visible but not larger than 2 centimeters (T3b) and bigger than 2 centimeters (T3c). This staging system also uses N categories to describe cancers that have or not spread to nearby lymph nodes. There are only two N categories, N0 which indicates that the cancerous tumors have not affected the lymph nodes, and N1 which indicates the involvement of lymph nodes close to the tumor. The M categories in the AJCC/TNM staging system provide information on whether the ovarian cancer has metastasized to distant organs such as liver or lungs. M0 indicates that the cancer did not spread to distant organs and M1 category is used for cancer that has spread to other organs of the body.

The AJCC/TNM staging system also contains a Tx and a Nx sub-category which indicates that the extent of the tumor cannot be described because of insufficient data, respectively the involvement of the lymph nodes cannot be described because of the same reason. The ovarian cancer stages are made up by combining the TNM categories in the following manner:

Stage I: T1+N0+M0; IA: T1a+N0+M0; IB: T1b+N0+M0; IC: T1c+N0+M0;
Stage II: T2+N0+M0; IIa: T2a+N0+M0; IIB: T2b+N0+M0; IIC: T2c+N0+M0;
Stage III: T3+N0+M0; IIIA: T3a+N0+M0; IIIB: T3b+N0+M0; IIIC: T3c+N0+M0 or Any T+N1+M0;
Stage IV: Any T+Any N+M1

In addition to being staged, like all cancers ovarian cancer is also graded. The histologic grade of a tumor measures how abnormal or malignant its cells look under the microscope. There are four grades indicating the likelihood of the cancer to spread and the higher the grade, the more likely for this to occur. Grade 0 is used to describe non-invasive tumors. Grade 0 cancers are also referred to as borderline tumors. Grade 1 tumors have cells that are well differentiated (look very similar to the normal tissue) and are the ones with the best prognosis. Grade 2 tumors are also called moderately well differentiated and they are made up by cells that resemble the normal tissue. Grade 3 tumors have the worst prognosis and their cells are abnormal, referred to as poorly differentiated.

However, there is a need for improved tools for the early detection; staging, grading and prognosis of cancer. In particular there is a need for predicting response to a cancer treatment.

SUMMARY OF THE INVENTION

Subject of the invention is a method for diagnosis of a cancer, comprising the steps of
(i) determining the level of antibodies against vascular endothelial growth factor (VEGF) in a sample from a subject to be diagnosed,
(ii) comparing the determined level in the sample to a control level of antibodies against VEGF (VEGF antibody control level) derived from subjects without cancer;
wherein a decreased level in the sample from the subject to be diagnosed as compared to the control level is indicative for cancer in the subject.

The invention further pertains to a method for diagnosis of a cancer, wherein the level of antibodies against vascular endothelial growth factor (VEGF) is determined in a sample from a subject to be diagnosed and wherein a level of anti-VEGF antibodies below 20 units/ml is indicative for cancer, preferably below 18 units/ml, more preferably below 15 units/ml, even more preferably below 14 units/ml, further preferred below 13.5 units/ml.

The present invention is further directed to an immunoassay method for detecting an anti-VEGF antibody in a sample from a subject, comprising the steps of
(a) contacting the sample suspected of comprising an anti-VEGF antibody with vascular endothelial growth factor (VEGF) or an antigenic peptide fragment thereof under conditions allowing for the formation of a complex between the anti-VEGF antibody with VEGF or the peptide fragment thereof,
(b) detecting the complex.

In the context of the present invention VEGF or an antigenic peptide fragment thereof can thus be used for the diagnosis of cancer.

The present invention further relates to research and/or diagnostic kit for the diagnosis of cancer or for the prediction of response or non-response in a patient, wherein the kit comprises vascular endothelial growth factor receptor (VEGF) or an antigenic (immunogenic) peptide fragment thereof.

The inventors also found that the level of antibodies against vascular endothelial growth factor (VEGF) correlates with the risk of relapse or mortality in subjects treated with an angiogenesis inhibitor. Decreased levels of anti-VEGF antibodies in samples correlated with a higher risk of relapse and/or mortality in patients treated with said or an angiogenesis inhibitor. Hence, levels of anti-VEGF antibodies in samples of patients to be treated with an angiogenesis inhibitor are an indicator for response or non-response of a patient, i.e. whether improvement of the disease is achieved in a patient (responder) or not (non-responder). If a patient responds to a treatment the disease is ameliorated. It might be the case that a patient responds to a treatment at first but suffers from relapse of the disease at a later stage. Also this is a form of non-response. However, it is difficult to predict whether a patient will respond or not to a treatment as it may be determined only at later stages with the known methods, e.g. when relapse, progression or death occurs. This problem is solved by the present invention as it provides a predictive method to predict whether a subject will respond or not to a certain treatment, e.g. a treatment with an angiogenesis inhibitor.

Therefore, the invention also relates to a method for determining whether a subject being treated or to be treated for cancer with a drug will respond to said treatment comprising the steps of
(i) determining the level of antibodies against vascular endothelial growth factor (VEGF) in a sample from said subject being treated or to be treated with a drug,
(ii) comparing the determined level in the sample to either one or both of a first and second VEGF antibody control level, wherein
  a) the first VEGF antibody control level is derived from subjects responding to said treatment, and
  b) the second VEGF antibody control level is derived from a subject not responding to said treatment,
wherein a decreased level in the sample from the subject being treated or to be treated as compared to the first VEGF antibody control level and/or an equal level as compared to the second VEGF antibody control level is indicative for a non-response of said subject to said treatment, and wherein an increased level in the sample from the subject being treated or to be treated as compared to the second VEGF antibody control level and/or an equal level as compared to the first VEGF antibody control level is indicative for a response of said subject to said treatment. In a preferred embodiment of the invention the subject is to be treated, i.e. the method to determine response of a subject is performed before the onset of treatment. In a preferred embodiment the drug is an angiogenesis inhibitor according to the present invention.

Furthermore, ratios may be used in order to determine response or non-response to a treatment with a drug, preferably an angiogenesis inhibitor as defined herein, preferably bevacizumab. In such embodiment a level of antibodies against VEGF in the sample from the subject to be treated of less than 0.9 fold as compared to the first VEGF antibody control level is indicative for a non-response of said subject to said treatment, preferably a level of antibodies against VEGF in the sample from the subject to be treated of less than 0.6 fold as compared to the first VEGF antibody control level is indicative for a non-response of said subject to said treatment, further preferred a level of antibodies against VEGF in the sample from the subject to be treated of less than 0.5 fold as compared to the first anti-VEGF control level is indicative for a non-response of said subject to said treatment. Likewise, ratios may be determined for the response. In such embodiment a level of antibodies against VEGF in the sample from the subject to be treated of more than 1.5 fold as compared to the second VEGF antibody control level is indicative for a response of said subject to said treatment, preferably a level of antibodies against VEGF in the sample from the subject to be treated of more than 1.9 fold as compared to the second VEGF antibody control level is indicative for a response of said subject to said treatment, further preferred a level of antibodies against VEGF in the sample from the subject to be treated of more than 2.0 fold as compared to the second anti-VEGF control level is indicative for a response of said subject to said treatment. The treatment and response preferably relate to an inhibitor of angiogenesis as defined herein, preferably bevacizumab.

The present invention also relates to a method of treating cancer in a subject, comprising determining the level of antibodies against vascular endothelial growth factor (VEGF) in a sample from the subject, wherein when the level of anti-VEGF antibodies in a sample from the subject is above 5.7, a chemotherapeutic drug/agent is administered to the subject. However, the threshold may also be determined as outlined above, hence, the method of treating cancer in a subject may also comprise the method for determining whether a subject being treated or to be treated for cancer with a drug will respond to said treatment, wherein the drug is administered if the determined levels of VEGF antibodies in said subject is indicative for response to the drug.

Furthermore, ratios may be determined when comparing the determined levels to the control levels. Hence, the invention also relates to a method of treating cancer in a subject with a drug, preferably an angiogenesis inhibitor, e.g. bevacizumab, comprising determining the level of antibodies against vascular endothelial growth factor (VEGF) in a sample from the subject to be treated and comparing the determined level in the sample to either one or both of a first and second VEGF antibody control level, wherein
 a) the first VEGF antibody control level is derived from subjects responding to said treatment, and
 b) the second VEGF antibody control level is derived from a subject not responding to said treatment,
wherein the drug is administered to the subject to be treated when a level of antibodies against VEGF in the sample from the subject to be treated of less than 0.9 fold, preferably less than 0.6 fold, more preferably less than 0.5 fold, as compared to the first VEGF antibody control level is determined, and/or when a level of antibodies against VEGF in the sample from the subject to be treated of more than 1.5 fold, preferably more than 1.9 fold, more preferably more than 2.0 fold, as compared to the second VEGF antibody control level is determined.

As outlined herein, results of non-response of a patient to a treatment may be relapse or progression of cancer, death (mortality) of the cancer. Hence, in a preferred embodiment of the method to determine/predict the response of a subject to a treatment the present invention also relates to a method for the prediction of risk stratification for relapse of cancer and/or mortality in a patient being treated or to be treated for cancer with a drug, the method comprising the steps of (i) determining the level of antibodies against vascular endothelial growth factor (VEGF) in a sample from said subject being treated or to be treated for cancer with said drug (ii) comparing the determined level in the sample to either one or both of a first and a second VEGF antibody control level, a) wherein the first VEGF antibody control level is derived from subjects not showing relapse or progression of cancer or mortality after treatment with said drug, and b) wherein the second VEGF antibody control level is derived from subjects showing relapse or progression of cancer or mortality after treatment with said drug, wherein a decreased level in the sample from the subject being treated or to be treated as compared to the first VEGF antibody control level and/or an equal level as compared to the second VEGF antibody control level is indicative for relapse or progression of cancer or mortality in the subject; and wherein an increased level in the sample from the subject being treated or to be treated as compared to the second VEGF antibody control level and/or an equal level as compared to the first VEGF antibody control level is indicative for no relapse and no progression of cancer and no mortality in the subject. Preferably the level in said patient is determined before the onset of treatment. The preferred subject is therefore in this context a subject to be treated with said drug. In a preferred embodiment of the present invention first VEGF antibody control level is derived from subjects that did not show relapse or progression of cancer or mortality within 20 months after onset of treatment with said drug and the second VEGF antibody control level is derived from subjects that did show relapse or progression of cancer or mortality within 20 months after onset of treatment with said drug.

The present invention also relates to a method prediction of risk stratification for relapse of cancer and/or mortality in a patient being treated or to be treated with a drug, comprising determining the level of antibodies against vascular endothelial growth factor (VEGF) in a sample from the subject, wherein when the level of anti-VEGF antibodies in a sample from the subject is below 25 units/ml, preferably below 20 units/ml, more preferred below 15 units/ml, is indicative for relapse or progression of cancer or mortality in the subject.

As will be readily understood by the skilled person, this method may be performed as a method for monitoring cancer treatment efficiency. In this embodiment the levels of anti-VEGF antibodies in said subject is determined during treatment, i.e. in a subject being treated with said drug.

DETAILED DESCRIPTION OF THE INVENTION

The present invention is based on the surprising finding of the inventors that in samples of patients with cancer (e.g. ovarian cancer) decreased levels of anti-VEGF antibodies can be found as compared to subjects without cancer. In other words the inventors have found that patients with cancer have little or no detectable antibodies against vascular endothelial growth factor (VEGF) in the blood (e.g. determined in serum) whereas in control groups anti-VEGF auto-antibodies can be detected at higher levels.

The present invention is based on the finding of that levels of autoimmune-antibodies in subjects have diagnostic and predictive properties. The antibodies to be detected in connection with the present invention are therefore autoantibody, i.e. those produced by immune system of the subject to be diagnosed or being or to be treated.

The invention relates to a method for the diagnosis of a cancer, comprising the steps of
(i) determining the level of antibodies against VEGF in a sample from a subject to be diagnosed,
(ii) comparing the determined level in the sample to a control level of antibodies against VEGF in samples derived from subjects without cancer;
wherein a decreased level in the sample from the subject to be diagnosed as compared to the control level is indicative for cancer in the subject.

Preferably, the cancer is an epithelial cancer, preferably selected from the group consisting of ovarian cancer, breast cancer, lung cancer, colon cancer, renal cancer, a glioblastoma and colorectal cancer. It will be understood by those of ordinary skills in the art, that if a preferred cancer is chose to be diagnosed, the control level should be derived from subjects without that specific cancer, i.e. if ovarian cancer is to be diagnosed, the control level shall be derived from subjects without ovarian cancer.

Figure 1:
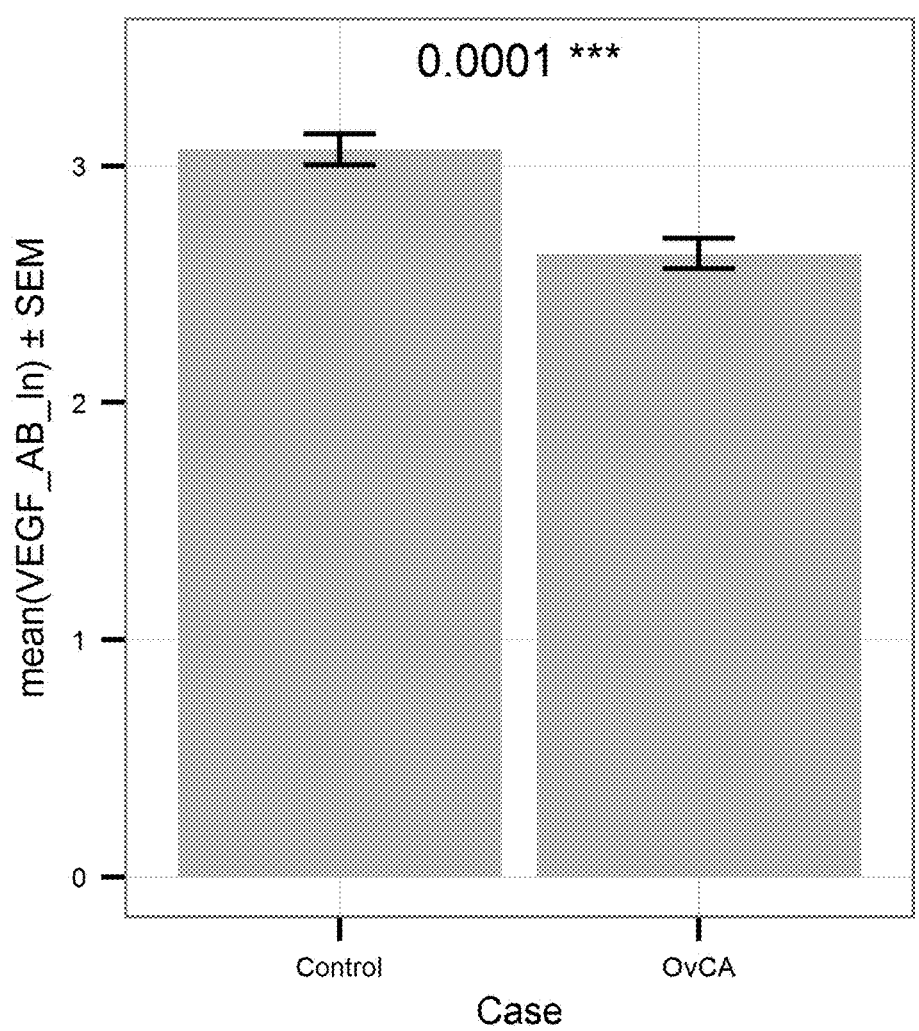
FIG. 1: Comparison of the mean level of anti-VEGF antibodies (ln of units/ml) in serum samples of ovarian cancer patients (OvCA; ln of mean=2.628; n=201) to the mean level of anti-VEGF antibodies in serum samples of a healthy control group (Control, ln of mean=3.007 units/ml; n=132). The p-value is indicated on top. Bars indicate standard error of mean.

As can be derived from FIG. 1, the ln of the mean level of VEGF antibodies in patients suffering from ovarian cancer is 2.628 (=13.85 units/ml) and in healthy subjects 3.007 (=20.23 units/ml). Hence, in one embodiment a level of less than 0.9 fold as compared to the control level from subjects without cancer is indicative for the presence of cancer, preferably a level of less than 0.8 fold, more preferably of less than 0.7 fold. The cancer is preferably a VEGF and VEGF-receptor (VEGFR) associated cancer as defined herein. Particularly preferred is ovarian cancer. The skilled person will acknowledge that in case a certain cancer is to be diagnosed, the control level is preferably derived from subjects not having this particular cancer.

The skilled artisan will understand that the diagnosis of cancer is performed in order to evaluate whether the patient is to be treated for cancer. Hence, in a preferred embodiment of the method for diagnosis, the subject to be diagnosed is treated for cancer if the VEGF antibody levels in said subject to be treated are indicative for the presence of cancer.

Auto-antibodies directed against VEGF are not known until today. The inventors of the present application for the first time demonstrate the presence of such antibodies as well as the diagnostic and predictive value. It was found that a decrease in the level of antibodies directed against VEGF in samples of a subject to be diagnosed as compared samples from subjects with proven absence of cancer is indicative for the presence of cancer as well as for the prediction of response or non-response to a treatment of the cancer with a drug. Hence, "cancer" in connection with the present invention is to be understood as any diseases involving unregulated cell growth. Cancer in this regard is a disease where cells divide and grow uncontrollably resulting in the formation of malignant tumors.

However, in a preferred embodiment of the present invention "cancer" refers to a VEGF and VEGF-receptor (VEGFR) associated cancer. VEGF and VEGFR associated cancers are known by the skilled person. VEGF has been implicated with poor prognosis in cancer. Numerous studies show a decreased overall survival and disease-free survival in those tumors overexpressing VEGF. The overexpression of VEGF may be an early step in the process of metastasis, a step that is involved in the "angiogenic" switch. Although VEGF has been correlated with poor survival, its exact mechanism of action in the progression of tumors remains unclear. Once released, VEGF elicits several responses. It causes a cell to survive, move, or further differentiate. Hence, VEGF is a target for the treatment of cancer. The first anti-VEGF drug, a monoclonal antibody named bevacizumab, was approved in 2004. Approximately 10-15% of patients benefit from bevacizumab therapy; however, biomarkers for bevacizumab efficacy are not yet known. Anti-VEGF therapies are important in the treatment of certain cancers. They involve monoclonal antibodies such as bevacizumab (Avastin), antibody derivatives such as ranibizumab (Lucentis), or orally-available small molecules that inhibit the tyrosine kinases stimulated by VEGF: lapatinib (Tykerb), sunitinib (Sutent), sorafenib (Nexavar), axitinib, and pazopanib. Some of these therapies target VEGF receptors rather than the VEGFs.

Hence, in a preferred embodiment of the present invention the cancer is selected from the group consisting of ovarian cancer, breast cancer, lung cancer, colon cancer, renal cancer, a glioblastoma and colorectal cancer. In a particularly preferred embodiment the cancer according to the present invention, including all embodiments, is an ovarian cancer. Ovarian cancer often derives from the epithelium of the ovary, but may also be derived from fallopian tube. However, it was found that in both cases the method of the present invention is predictive for the presence of cancer or the response to a certain treatment. Hence, in one embodiment of the present invention cancer is an ovarian cancer, the ovarian cancer being epithelial ovarian cancer or cancer derived from the fallopian tube.

The skilled person knows that depending on the subject, different cancers may be diagnosed. He is aware that he also may have to consider further parameters to diagnose the subject, e.g. when diagnosing ovarian cancer, the subject has to be female. In the context of the present invention the subject to be diagnosed is a mammal, preferably a human. In a further preferred embodiment the subject is a female mammal, preferably a female human subject suspected of having ovarian cancer or a female mammal, preferably a female human subject to be screened for the presence of ovarian cancer, preferably a female human subject to be treated or being treated for ovarian cancer with a drug.

The invention particularly relates to a method for diagnosis of ovarian cancer, wherein the level of antibodies against VEGF is determined in a sample from a subject to be diagnosed and wherein a level of anti-VEGF antibodies below 20 units/ml is indicative for ovarian cancer, preferably below 18 units/ml, more preferably below 15 units/ml, even more preferably below 14 units/ml, further preferred below 13.5 units/ml.

In the context of the present invention the terms "VEGF" or "factor" relates to the "vascular endothelial growth factor"

Vascular endothelial growth factor (VEGF) is a signal protein stimulating vasculogenesis and angiogenesis. VEGF's normal function is to create new blood vessels during embryonic development, new blood vessels after injury, muscle following exercise, and new vessels (collateral circulation) to bypass blocked vessels. Overexpression or missregulation of VEGF contributes to diseases. Cancers in order to allow growth beyond a certain size need supply blood. Many tumors express VEGF in order to grow and metastasize. Overexpression of VEGF can cause vascular disease in the retina of the eye and other parts of the body. Drugs such as bevacizumab and other angiogenesis inhibitors can inhibit VEGF and control or slow those diseases.

VEGF is a sub-family of growth factors, to be specific, the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature). VEGF includes VEGF-A, VEGF-B, VEGF-C, VEGF-D and Placenta growth factor (PlGF). Before the discovery of VEGF-B to D and PlGF, VEGF-A was the only known VEGF. VEGF-A was called just VEGF at these days. These VEGF subtypes have similar activities. However, VEGF-A plays crucial roles in angiogenesis, migration of endothelial cells, mitosis of endothelial cells, methane monooxygenase activity, $\alpha v \beta 3$ activity, creation of blood vessel lumen, creates fenestrations, chemotactic for macrophages and granulocytes, vasodilation (indirectly by NO release). VEGF-B is particularly involved in embryonic angiogenesis (myocardial tissue, specifically) (Claesson-Welsh, L. (2008). "VEGF-B Taken to Our Hearts: Specific Effect of VEGF-B in Myocardial Ischemia". Arteriosclerosis, Thrombosis, and Vascular Biology 28 (9): 1575-1576). VEGF-C regulates lymphangiogenesis, while VEGF-D is needed for the development of lymphatic vasculature surrounding lung bronchioles. Recently, VEGF-C has been shown to be an important inducer of neurogenesis in the murine subventricular zone, without exerting angiogenic effects (Shin, Y. J., J. S. Choi, et al. (2010). "Induction of vascular endothelial growth factor receptor-3 mRNA in glial cells following focal cerebral ischemia in rats." J Neuroimmunol 229(1-2): 81-90). PlGF is important for vasculogenesis, and also needed for angiogenesis during ischemia, inflammation, wound healing, and cancer.

The term 'VEGF' covers a number of proteins from two families, that result from alternate splicing of mRNA from a single, 8-exon, VEGF gene. In addition to the above nomenclature a parallel nomenclature exists. The two different families are referred to according to their terminal exon (exon 8) splice site—the proximal splice site (denoted VEGFxxx) or distal splice site (VEGFxxxb). In addition, alternate splicing of exon 6 and 7 alters their heparin-binding affinity, and amino acid number (in humans: VEGF121, VEGF121b, VEGF145, VEGF165, VEGF165b, VEGF189, VEGF206; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF receptors (VEGFRs) (A VEGF-A splice variant defective for heparan sulfate and neuropilin-1 binding shows attenuated signaling through VEGFR-2 doi: 10.1007/s00018-006-6254-9).

However, VEGF in context with the present invention refers to any of the VEGF subtypes outlined above. In a preferred embodiment the VEGF according to the resent invention is selected from the group consisting of VEGF-A, VEGF-B, VEGF-C, VEGF-D and PlGF. Preferred VEGF according to the invention is VEGF-A, preferably VEGF165 according to SEQ ID NO:1. Hence, the anti-VEGF antibodies in the samples as mentioned herein preferably bind to one or any VEGF-A, preferably to VEGF165, preferably to protein comprising SEQ ID NO:1.

In the context of the immunoassays of the present invention the "VEGF" may be present in its natural cellular environment and can be used together with the material associated with VEGF in its natural state as well as in isolated form with respect to its primary, secondary and tertiary structures. The VEGF is well known to those skilled in the art. The factor is preferably used in isolated form, i.e. essentially free of other proteins, lipids, carbohydrates or other substances naturally associated with VEGF. "Essentially free of" means that the factor is at least 75%, preferably at least 85%, more preferably at least 95% and especially preferably at least 99% free of other proteins, lipids, carbohydrates or other substances naturally associated with the factor.

In connection with the present invention, the naturally occurring factor as well as all modifications, mutants or derivatives of the VEGF can be used. Similarly, a VEGF produced by means of recombinant techniques, which includes amino acid modifications, such as inversions, deletions, insertions, additions etc. can be used according to the invention provided that this part of the essential function of the VEGF is present, namely the capability of binding antibodies. The VEGF being used may also comprise exceptional amino acids and/or modifications of such as alkylation, oxidation, thiol-modification, denaturation, oligomerization and the like. The VEGF can also be synthesized by chemical means. According to the invention the VEGF particularly can be a protein and/or peptide or a fusion protein, which in addition to other proteins, peptides or fragments thereof, includes the VEGF as a whole or in part. Using conventional methods, peptides or polypeptides of the VEGF which have functionally analogs, analogous properties can be determined by those skilled in the art. For example such polypeptides or peptides have 50-60%, 70% or 80%, preferably 90%, more preferably 95%, and most preferably 98% sequence homology to peptides identified as VEGF, and said homology can be determined, e.g. by means of Smith-Waterman homology search algorithm, using the MPFRCH program (Oxford Molecular), for example.

The term "peptide" or "polypeptide" of an VEGF used in the present invention, comprises also molecules differing from the original sequence by deletion(s), insertion(s), substitution(s) and/or other modifications well known in the prior art and/or comprising a fragment of the original amino acid molecule, the VEGF still exhibiting the properties mentioned above. Such a peptide has preferably at least a length of 100 amino acid residues but may also be shorter, e.g. at least 12, 15, 20 or 25 amino acid residues in length. Also included are allele variants and modifications. Methods of producing the above changes in the amino acid sequence are well known to those skilled in the art and have been described in the standard textbooks of molecular biology, e.g. Sambrook et al., supra. Those skilled in the art will also be able to determine whether a VEGF, thus, modified still has the properties mentioned above. The amino acid sequence of VEGF is known. Database entries exist in several well known Databases. When referring to the amino acid sequence of VEGF any amino acid sequence known is meant, particularly those disclosed in common databases, preferably of human origin, preferably human VEGF-A, preferably human VEGF165, preferably comprising SEQ ID NO:1, more preferably comprising amino acids 27 to 191 of SEQ ID NO:1. The VEGF may be glycosylated in vivo. In the present specification all of the above illustrated modifications of the VEGF will be referred to as "functionally analogous peptides or proteins" in brief.

The antibodies to be detected or determined according to the present invention are directed against VEGF. This means that the antibodies specifically bind VEGF. Specific binding of an antibody normally occurs via binding of a binding site of the antigen. The antibodies of the present invention are those specifically binding to VEGF or immunogenic fragments thereof. This binding may occur via recognition of sequence or structural epitopes. The skilled person is aware of methods of how to determine specific epitopes, e.g. fragments of the antigen VEGF, which are recognized and bound by the antibodies to be determined. Fragments of VEGF binding to the auto antibodies are called immunogenic or antigenic fragments. Methods for determining fragments of an antigen binding the antibody are described in several publications (e.g. Gershoni, J M; Roitburd-Berman, A; Siman-Tov, D D; Tarnovitski Freund, N; Weiss, Y (2007). "Epitope mapping: The first step in developing epitope-based vaccines". BioDrugs 21 (3): 145-56; Westwood, M R; Hay, F C (2001). Epitope Mapping: a practical approach. Oxford, Oxfordshire: Oxford University Press. ISBN 0-19-963652-4; Flanagan et al. (2011), "Mapping Epitopes with H/D-Ex Mass Spec". Genetic Engineering and Biotechnology news; 31(1); Gaseitsiwe, S.; Valentini, D.; Mandavifar, S.; Reilly, M.; Ehrnst, A.; Maeurer, M. (2009) "Peptide Microarray-Based Identification of *Mycobacterium tuberculosis* Epitope Binding to HLA-DRB1*0101, DRB1*1501, and DRB1*0401". Clinical and Vaccine Immunology 17 (1): 168-75; Linnebacher, Michael; Lorenz, Peter; Koy, Cornelia; Jahnke, Annika; Born, Nadine; Steinbeck, Felix; Wollbold, Johannes; Latzkow, Tobias et al. (2012). "Clonality characterization of natural epitope-specific antibodies against the tumor-related antigen topoisomerase IIa by peptide chip and proteome analysis: A pilot study with colorectal carcinoma patient samples" Analytical and Bioanalytical Chemistry 403 (1): 227-38; Cragg, M. S. (2011). "CD20 antibodies: Doing the time warp". Blood 118 (2): 219-20; Banik, Soma S. R.; Doranz, Benjamin J. (2010). "Mapping Complex Antibody Epitopes". Genetic Engineering and Biotechnology News 3 (2): 25-8; and Paes, Cheryl; Ingalls, Jada; Kampani, Karan; Sulli, Chidananda; Kakkar, Esha; Murray, Meredith; Kotelnikov, Valery; Greene, Tiffani A. et al. (2009). "Atomic-Level Mapping of Antibody Epitopes on a GPCR". Journal of the American Chemical Society 131 (20): 6952-4). In context with the present invention anti-VEGF antibodies are understood as any immunoglobulin specifically recognizing/binding to VEGF, preferably VEGF-A. The antibody in a preferred embodiment binds VEGF-A, preferably to VEGF165, preferably to a protein comprising of consisting of an amino acid sequence according to SEQ ID NO:1, preferably to amino acids 27 to 191 of SEQ ID NO:1.

In the context of the present invention the anti-VEGF antibody may particularly be selected from the group of IgA-antibody, IgG-antibody and IgM-antibody, preferably an IgG antibody, e.g. IgG1, IgG2, IgG3 and IgG4.

Herein, the sample of the subject to be diagnosed in which the level of anti-VEGF antibodies is to be determined is preferably a bodily fluid such as whole blood or lymph or fractions of blood such as serum or plasma. Preferably in the context of the present invention the sample is plasma or serum.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

The control levels as disclosed herein refer to control levels of VEGF antibodies. It will be readily understood by the skilled person that the control levels from subjects having the desired disease or response as defined in the methods and to which the determined levels are compared to, are not necessarily determined in parallel but may be represented by previously determined levels. Nevertheless, control levels may be determined in parallel. The skilled person with the disclosure of the present invention and his knowledge is able to determine such levels, as will be outlined herein below. Hence, the control levels of the present invention may be previously defined thresholds. Preferred thresholds are disclosed herein. Furthermore, it will be acknowledged by the skilled person that control levels are, like the levels to be determined in the subject to be diagnosed or treated, determined in samples of the recited subjects having the desired disease or response or being healthy. Preferably, the sample is the same kind of sample as the sample of the person to be diagnosed or to be treated, e.g. when the sample of the latter is serum, the control levels are preferably determined in serum samples derived from the control subjects.

Figure 6:
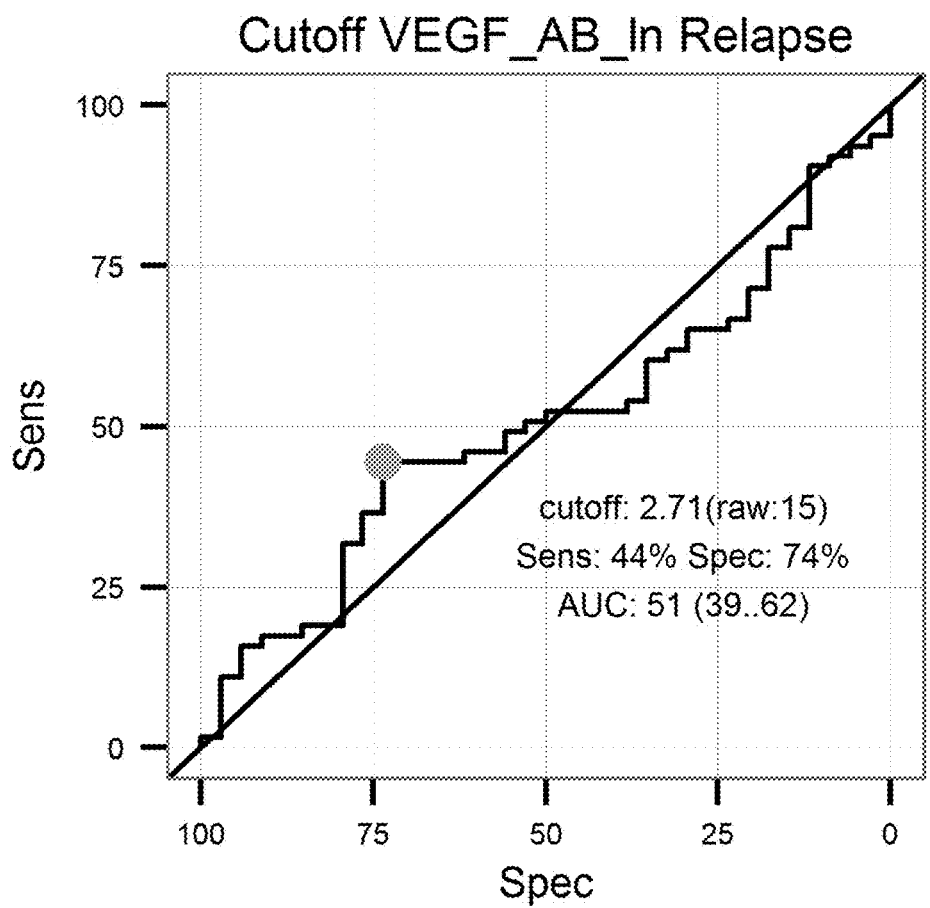
FIG. 6: A: on top sensitivity of the prediction of relapse of ovarian cancer after surgical treatment and treatment with a platinum analogue is plotted against the specificity. Cutoff value (2.71 units/ml) and AUC is given in the graph. Below the proportion of patients not showing relapse after surgical treatment and treatment with a platinum analogue is shown over the time for patients having antibody levels below the ROC-cutoff value (dotted line) and above the ROC-cutoff value (solid line). B: on top sensitivity of the prediction of survival after surgical treatment and treatment with a platinum analogue is plotted against the specificity. Cutoff value (2.34 units/ml) and AUC is given in the graph. Below the proportion of patients surviving after surgical treatment and treatment with a platinum analogue is shown over the time for patients having antibody levels below the ROC-cutoff value (dotted line) and above the ROC-cutoff value (solid line). C: on the left sensitivity of the prediction of a combined endpoint (death or relapse of cancer) of ovarian cancer patients after surgical treatment and treatment with a platinum analogue is plotted against the specificity. Cutoff value (1.16 units/ml) and AUC is given in the graph. Below the proportion of patients surviving or not showing relapse of cancer after surgical treatment and treatment with a platinum analogue is shown over the time for patients having antibody levels below the ROC-cutoff value (dotted line) and above the ROC-cutoff value (solid line).
Figure 6:
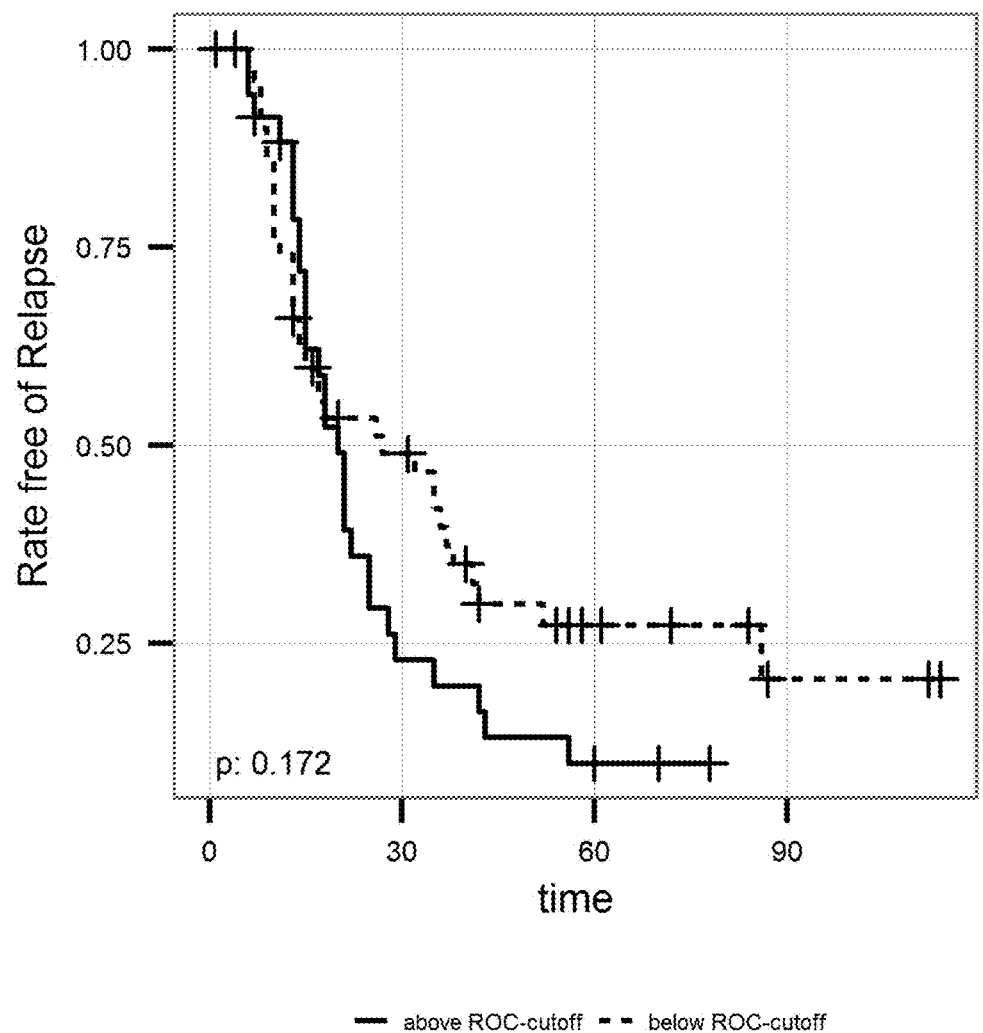
Figure 6:
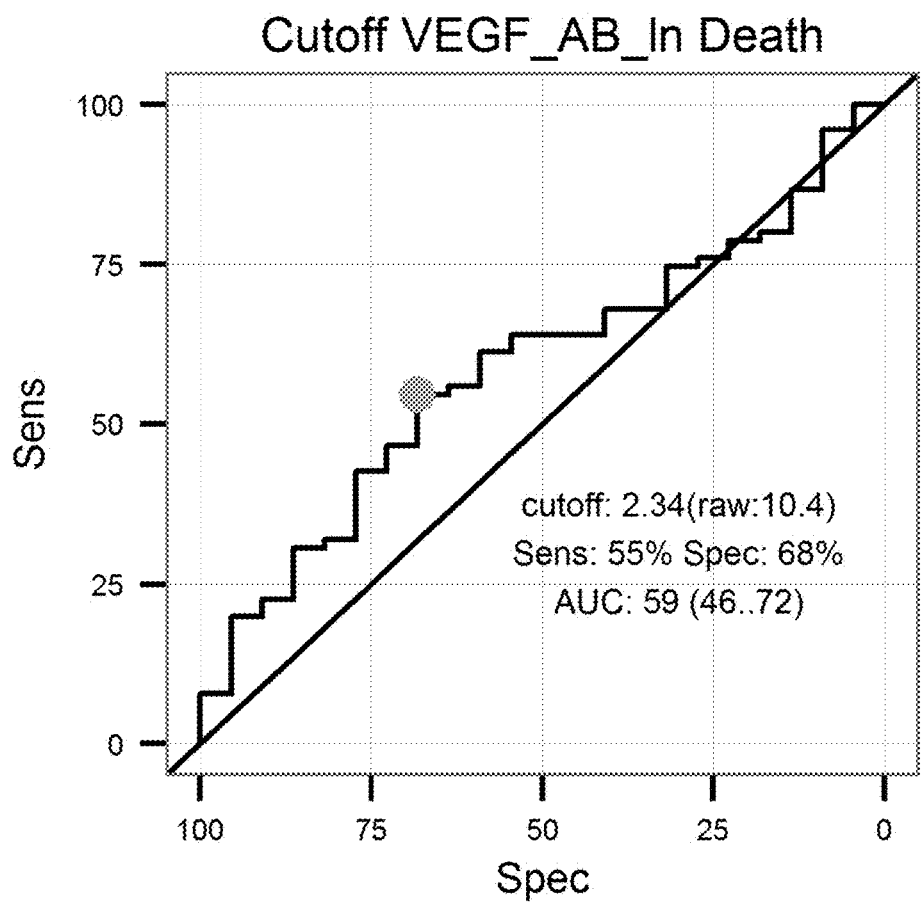
Figure 6:
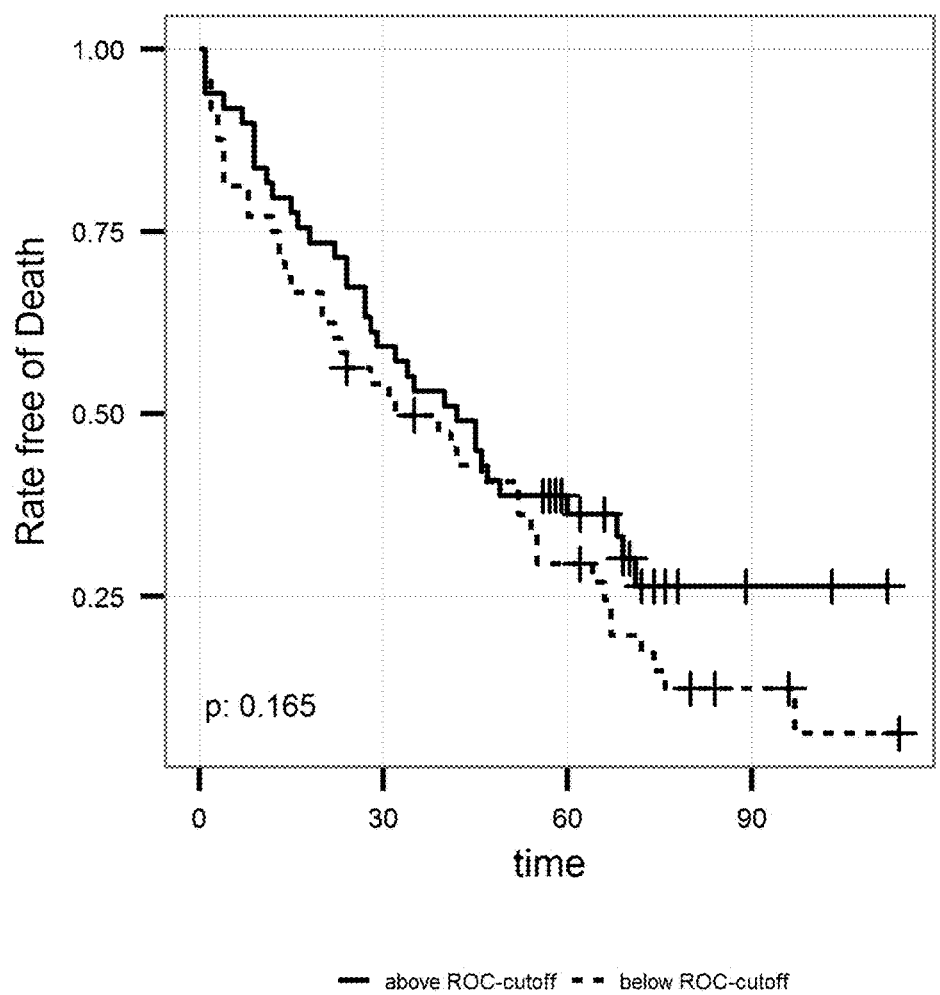
Figure 6:
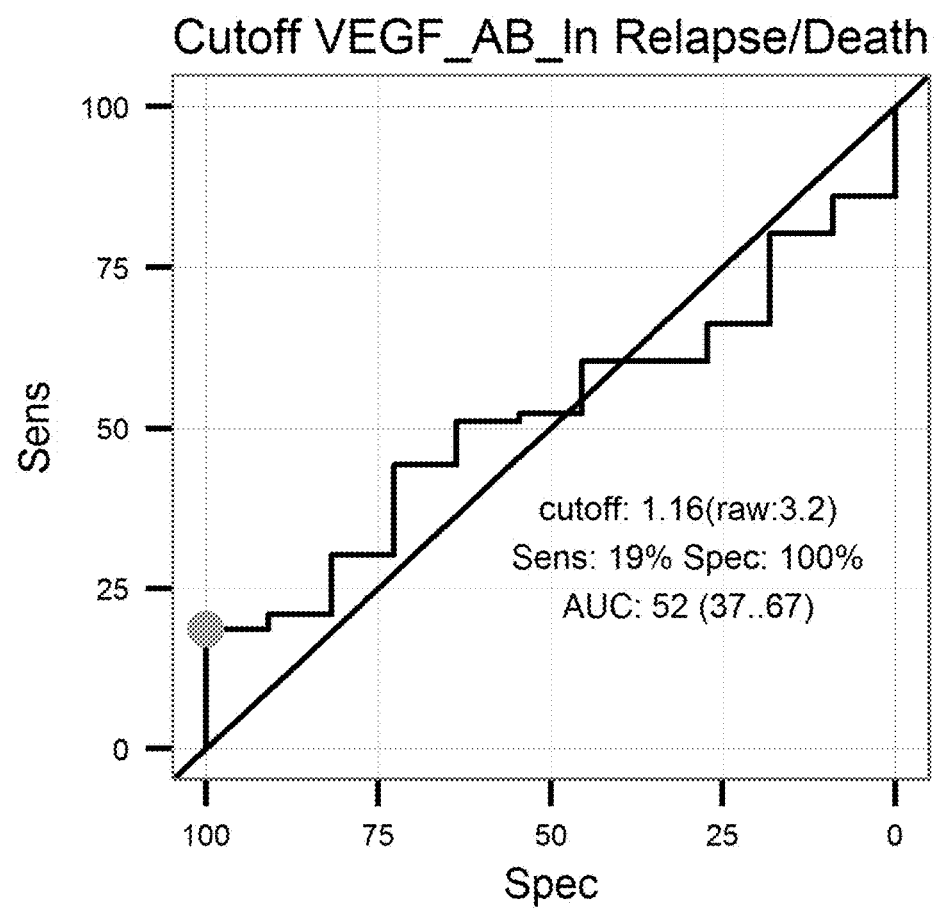
Figure 6:
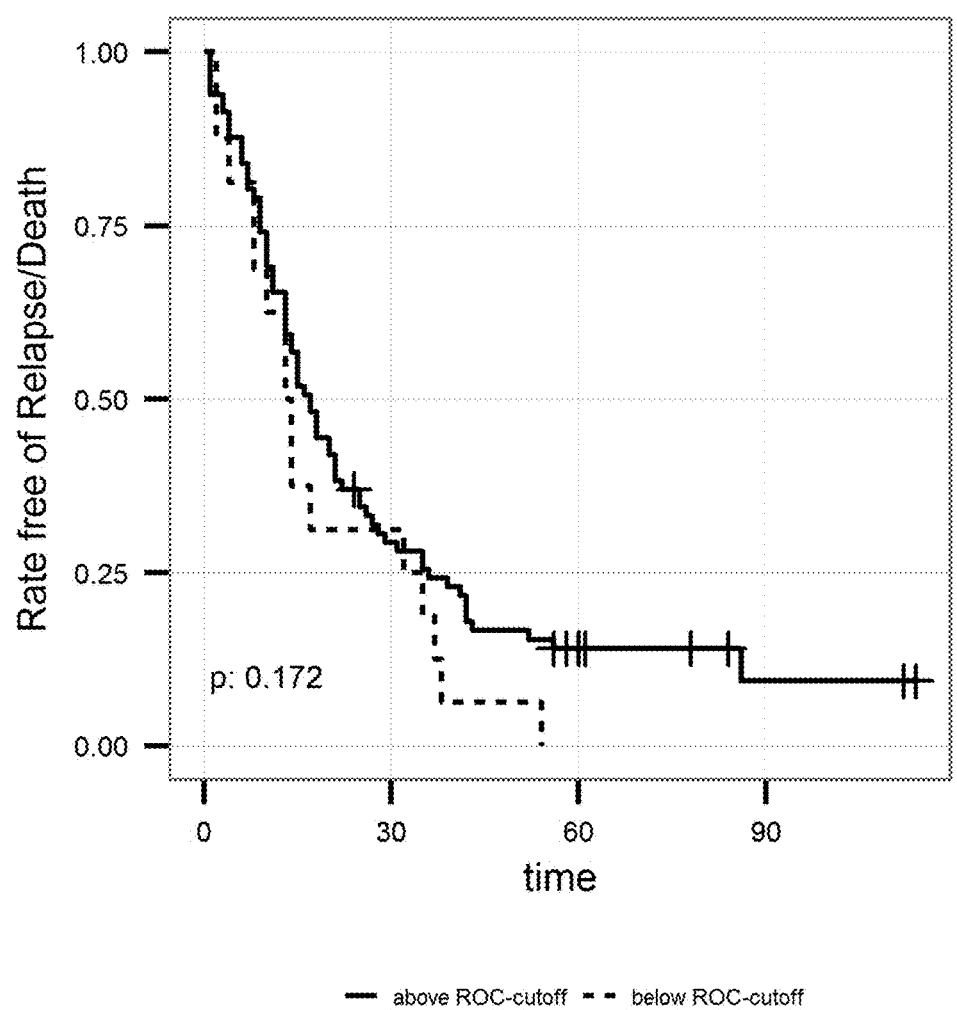

As outlined herein, the levels of VEGF antibodies in samples of the patient to be diagnosed and treated or to be treated are compared with the control groups as defined herein. However, in one embodiment the levels are compared to fixed values, i.e. thresholds under or over which a certain diagnosis, or prognosis of response is given. To this end, unit-standards may be applied. The present inventors set out such standard for the VEGF using serum samples from systemic sclerosis patients. Systemic sclerosis patients are known to have high levels of autoimmune antibodies in general. Hence, the inventors took a serum sample of a systemic sclerosis patient. However, it will be acknowledged by the skilled person that also other samples may be taken to set a different standard, e.g. samples of healthy subjects, samples of cancer patients. Nevertheless the principle of generating a standard (units) is the same in any case and are exemplified herein using serum samples of systemic sclerosis patients. In the context of the present invention "units/ml", unless specified otherwise, refers to the concentration of antibodies standardised as exemplified herein. Hence, in one embodiment of the present invention 50 units/ml refers to a dilution of 1:400 of a serum sample of systemic sclerosis patients. The serum sample may be derived from a single patient or of a cohort of a plurality of patients, e.g. a cohort of 200 patients suffering from systemic sclerosis. The present inventors found that the concentration of VEGF antibodies in samples of systemic sclerosis do not differ by more than about 10%, showing such standard being reproducible. In one preferred embodiment the standard for the concentrations of the autoimmune antibodies is generated in the following way: a serum sample of a systemic sclerosis patient (or a larger cohort) is diluted (a) 1:400 for standard point 50 Units/ml, (b) 1:800 for standard point 25 Units/ml, (c) 1:1600 for standard point 12.5 Units/ml, (d) 1:3200 for standard point 6.25 Units/ml, (e) 1:6400 for standard point 3.13 Units/ml and (f) 1:12800 for standard point 1.56 Units/ml. These standards are then used for the immunoassay chosen, e.g. ELISA, and then correlated with the respective read-out value, e.g. for ELISA optical density at 450 nm/optical density at 620 nm. A typical standard curve of a VEGF auto-antibody ELISA is shown in FIG. 6. Nevertheless, the skilled person will readily understand that it may also be possible to standardize the levels of VEGF-autoantibodies using different samples, e.g. samples of healthy subjects or cancer patients.

"equal" level in context with the present invention means that the levels differ by not more than ±10%, preferably by not more than ±5%, more preferably by not more than ±2%. "Decreased" or "increased" level in the context of the present invention mean that the levels differ by more than 10%, preferably by more than 15%, preferably more than 20%.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

"Serum" is the liquid fraction of whole blood that is collected after the blood is allowed to clot. When coagulated blood (clotted blood) is centrifuged serum can be obtained as supernatant. It does not contain fibrinogen, although some clotting factors remain.

In the method of the present invention, the anti-VEGF antibody is preferably detected in an immunoassay. Suitable immunoassays may be selected from the group of immunoprecipitation, enzyme immunoassay (EIA)), enzyme-linked immunosorben assays (ELISA), radioimmunoassay (RIA), fluorescent immunoassay, a chemiluminescent assay, an agglutination assay, nephelometric assay, turbidimetric assay, a Western Blot, a competitive immunoassay, a non-competitive immunoassay, a homogeneous immunoassay a heterogeneous immunoassay, a bioassay and a reporter assay such as a luciferase assay. Preferably herein the immunoassay is an enzyme linked immunosorbent assay (ELISA).

The immunoassays can be homogenous or heterogeneous assays, competitive and non-competitive assays. In a particularly preferred embodiment, the assay is in the form of a sandwich assay, which is a non-competitive immunoassay, wherein the anti-VEGF antibody (i.e. the "analyte") to be detected and/or quantified is allowed to bind to an immobilized VEGF protein or immunogenic peptide fragment thereof and to a secondary antibody. The VEGF or fragment thereof (i.e. a peptide), may e.g., be bound to a solid phase, e.g. a bead, a surface of a well or other container, a chip or a strip, and the secondary antibody is an antibody which is labeled, e.g. with a dye, with a radioisotope, or a reactive or catalytically active moiety such as a peroxidase, e.g. horseradish peroxidase. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference). Sandwich immunoassays can for example be designed as one-step assays or as two-step assays.

The detectable label may for example be based on fluorescence or chemiluminescence. The labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in *Kirk-Othmer, Encyclopedia of chemical technology*, 4$^{th}$ ed., executive editor, J. I. Kroschwitz; editor, M. Howe-Grant, John Wiley & Sons, 1993, vol. 15, p. 518-562, incorporated herein by reference, including citations on pages 551-562. Preferred chemiluminescent dyes are acridiniumesters.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive the immunoassay is. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

An "immunogenic peptide" or "antigenic peptide" as used herein is a portion of an VEGF protein that is recognized (i.e., specifically bound) by the anti-VEGF antibody. Such immunogenic peptides generally comprise at least 5 amino acid residues, more preferably at least 10, and still more preferably at least 20 amino acid residues of EGF. However, they may also comprise at least 30, 40, 50, 60, 70, 80, 90, 100, 110, 120, 130, 140 or 150 amino acid residues.

For the purposes of the immunoassays and diagnostic methods of the invention VEGF by expression in cells, preferably eukaryotic cells or in cell free, preferably eukaryotic cell free systems. Hence, in the assays and methods of the invention VEGF may be present in its natural cellular environment and can be used together with the material associated with the factor in its natural state as well as in isolated form. Suitable expression systems include Chinese hamster ovary (CHO) cells overexpressing the human VEGF. Hence, cell extracts (particularly extracts from CHO cells overexpressing the human VEGF) can be used to detect anti-VEGF antibodies. Based on the weight of the whole receptor in the preparation (e.g. the "extract") to be used according to the invention, the isolated factor should account for at least 0.5%, preferably at least 5% more preferably at least 25%, and in a particular preferred embodiment at least 50%. The receptor is preferably used in isolated form, i.e. essentially free of other proteins, lipids, carbohydrates or other substances naturally associated with the receptor. "Essentially free of" means that the receptor is at least 75%, preferably at least 85%, more preferably at least 95% and especially preferably at least 99% free of other proteins, lipids, carbohydrates or other substances naturally associated with the factor.

In particular, the method of the present invention comprises the steps of
(a) contacting the sample with VEGF or an antigenic peptide fragment under conditions allowing for the formation of a complex between anti-VEGF antibodies with VEGF or the antigenic peptide fragment thereof,
(b) detecting the complex.

Hence, the invention relates to an immunoassay method for detecting an anti-VEGF antibody in a sample from a subject, comprising the steps of
(a) contacting the sample suspected of comprising an anti-VEGF antibody with VEGF or an antigenic peptide fragment thereof under conditions allowing for the formation of a complex between the anti-VEGF antibody with VEGF or the antigenic peptide fragment thereof,
(b) detecting the complex.

The VEGF or the antigenic peptide fragment thereof may preferably be immobilized on a surface. The complex may for example be detected using a secondary antibody against the Fc portion of the anti-VEGF antibody. When the anti-VEGF antibody is an IgG-antibody, the secondary antibody may be an anti-IgG antibody. In a particular embodiment, the subject is a human and
(i) the anti-VEGF antibody is a IgG1-antibody and the secondary antibody is an anti-human-IgG1 antibody; or
(ii) the anti-VEGF antibody is a IgG2-antibody and the secondary antibody is an anti-human-IgG2 antibody; or
(iii) the anti-VEGF antibody is a IgG3-antibody and the secondary antibody is an anti-human-IgG3 antibody; or
(iv) the anti-VEGF antibody is a IgG4-antibody and the secondary antibody is an anti-human-IgG4 antibody.

The secondary antibody may for example be labeled with a detectable marker, e.g. a peroxidase.

Furthermore, in the methods of the present invention further parameters of the subject may be considered as well for diagnosis, differential diagnosis, prognosis of response etc. Such parameters in a multivariate model may include gender, age, histological evaluation, Figo or histopathological staging, grading of the tumor and other markers. Dependent variables for determining survival may also be time till death, time till first relapse, time till death or first relapse (shorter interval if both events occurred). A Cox-Proportional-Hazard regression predicts the dependent variable based on one or more independent variables. These predictors can either be measures (as e.g. level of a biomarker) or categorical data (as e.g. response to a previous treatment). The skilled person is aware of the fact that diagnostic markers only give a certain degree of sensitivity and specificity, as also outlined herein. He knows that different further parameters might be considered in order to increase both. For example, when detecting levels of a marker indicative for epithelial cancer, inter alia ovarian cancer, the skilled person would not diagnose ovarian cancer in a male human subject. Nevertheless, the present invention provides a new and superior marker for diagnosis, prognosis of cancer, particularly for ovarian cancer. In the context of the methods of the invention and particularly the immunoassays of the invention, the presence of one or more further diagnostic markers for ovarian cancer is detected in the sample. For example, in a diagnostic method of the present invention levels of CA125, Human Epidymis Protein 4 (HE4) and/or Mesothelin are detected in addition.

The invention also relates to the use of VEGF or an antigenic peptide fragment thereof, preferably as set out herein above, for the diagnosis of cancer, preferably for the diagnosis of an VEGF or VEGFR associated cancer, more preferably for the diagnosis of a cancer selected from the group consisting of ovarian cancer, lung cancer, renal cancer, colon cancer, and colorectal cancer.

In the context of the present invention, the levels of the anti-VEGF antibodies a may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy individuals not having ovarian cancer) and "disease" populations. For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, below which the test is considered to be abnormal and above which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art. See, e.g., Hanley et al. 1982. Radiology 143: 29-36. Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

In other embodiments, a positive likelihood ratio, negative likelihood ratio, odds ratio, or hazard ratio is used as a measure of a test's ability to predict risk or diagnose a disease. In the case of a positive likelihood ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group. In the case of a negative likelihood ratio, a value of 1 indicates that a negative result is equally likely among subjects in both the "diseased" and "control" groups; a value greater than 1 indicates that a negative result is more likely in the test group; and a value less than 1 indicates that a negative result is more likely in the control group.

In the case of an odds ratio, a value of 1 indicates that a positive result is equally likely among subjects in both the "diseased" and "control" groups; a value greater than 1 indicates that a positive result is more likely in the diseased group; and a value less than 1 indicates that a positive result is more likely in the control group.

In the case of a hazard ratio, a value of 1 indicates that the relative risk of an endpoint (e.g., death) is equal in both the "diseased" and "control" groups; a value greater than 1 indicates that the risk is greater in the diseased group; and a value less than 1 indicates that the risk is greater in the control group.

The skilled artisan will understand that associating a diagnostic or prognostic indicator, with a diagnosis or with a prognostic risk of a future clinical outcome is a statistical analysis. For example, a marker level of lower than X may signal that a patient is more likely to suffer from an adverse outcome than patients with a level more than or equal to X, as determined by a level of statistical significance. Additionally, a change in marker concentration from baseline levels may be reflective of patient prognosis, and the degree of change in marker level may be related to the severity of adverse events. Statistical significance is often determined by comparing two or more populations, and determining a confidence interval and/or a p value. See, e.g., Dowdy and Wearden, *Statistics for Research*, John Wiley & Sons, New York, 1983. Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

Suitable threshold levels for the stratification of subjects into different groups (categories) have to be determined for each particular combination of VEGF-antibodies, disease and/or medication. This can e.g. be done by grouping a reference population of patients according to their level of VEGF-antibodies into certain quantiles, e.g. quartiles, quintiles or even according to suitable percentiles. For each of the quantiles or groups above and below certain percentiles, hazard ratios can be calculated comparing the risk for an adverse outcome, i.e. an "cancer" or a "non response", e.g. in terms of survival rate/mortality, between those patients who have received a certain medication and those who did not, or in terms of presence and absence of cancer in patients. In such a scenario, a hazard ratio (HR) above 1 indicates a higher risk for an adverse outcome for the patients who have received a treatment than for patients who did not. A HR below 1 indicates beneficial effects of a certain treatment in the group of patients. A HR around 1 (e.g. +/−0.1) indicates no elevated risk but also no benefit from medication for the particular group of patients. By comparison of the HR between certain quantiles of patients with each other and with the HR of the overall population of patients, it is possible to identify those quantiles of patients who have an elevated risk and those who benefit from medication and thereby stratify subjects according to the present invention.

In some cases presence of cancer, relapse and/or mortality upon treatment with an angiogenesis inhibitor will affect patients with high levels (e.g. in the fifth quintile) of VEGF-antibodies, while in other cases only patients with low levels of VEGF-antibodies will be affected (e.g. in the first quintile). However, with the above explanations, a skilled person is able to identify those groups of patients having cancer, those groups that do respond to a medication and those groups that do not respond to the medication. Exemplarily, some combinations of hormones and medications are listed for several diseases in the appended examples. In another embodiment of the invention, the diagnosis, risk for relapse of cancer and/or mortality and/or outcome for a patient are determined by relating the patient's individual level of marker peptide to certain percentiles (e.g. 97.5th percentile) of a healthy population.

Kaplan-Meier estimators may be used for the assessment or prediction of the outcome or risk (e.g. diagnosis, relapse, progression or morbidity) of a patient.

The invention also pertains to a research and/or diagnostic kit for the diagnosis of cancer, e.g. ovarian cancer, or for the prediction of risk stratification for relapse of cancer and/or mortality in a patient, wherein the kit comprises VEGF or an antigenic peptide fragment thereof. The kit may further comprise an antibody directed to the Fc portion of the anti-VEGF antibody to be detected, i.e. an anti-human IgG antibody.

Such kits can comprise a carrier, package or container that is compartmentalized to receive one or more containers such as vials, tubes, and the like, each of the container(s) comprising one of the separate elements to be used in the method. The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific therapeutic or non-therapeutic application, and can also indicate directions for either in vivo or in vitro use, such as those described herein. Directions and or other information can also be included on an insert which is included with the kit.

The term "drug" in connection with the present invention is to be understood as any substance, pharmaceutical composition or the like which are intended for the treatment of cancer, preferably an VEGF or VEGFR associated cancer as outlined herein, particularly preferred ovarian cancer. Different drugs are known. Preferred drugs are angiogenesis inhibitors, preferably VEGF or VEGFR inhibitors. Drugs used in the treatment of cancer include therapeutic antibodies such as bevacizumab (sold as Avastin® by Roche), cetuximab, zalutumumab, nimotuzumab, and matuzumab, and are preferably selected from this group. In a preferred embodiment the drug used for the treatment of cancer are drugs directed against angiogenesis, i.e. angiogenesis inhibitors. Angiogenesis is a physiological process through which new blood vessels form from pre-existing vessels and plays a fundamental role in the transition of tumors from a benign state to a malignant one. Angiogenesis inhibitors are therefore well known drugs for the treatment of cancer and are preferred in the present invention. They include and are preferably selected from the group consisting of bevacizumab and Aflibercept (also known as Zaltrap). Bevacizumab (Trade name Avastin®, Roche) is a particularly preferred drug according to the present invention and is slows the growth of new blood vessels. It is licensed to treat various cancers, including ovarian cancer, colorectal cancer, colon cancer, lung cancer, breast cancer, glioblastoma, kidney (renal) renal, pancreatic cancer, prostate cancer, gastric cancer, and liver cancer. In a preferred embodiment the angiogenesis inhibitor is bevacizumab. Furthermore, "drug" also refers to chemotherapeutic agents. Preferred chemotherapeutic agents are platinum analogues used for treating cancer. Such platinum analogues are known by the skilled person and are preferably selected form the group consisting of cisplatin, carboplatin, oxaliplatin, satraplatin, and triplatin-tetranitrate, preferably cisplatin or carboplatin.

Also encompassed by the invention is a method of treating cancer with a drug in a subject, comprising determining the level of antibodies against VEGF in a sample from the subject, wherein when the level of anti-VEGF antibodies in a sample from the subject is above a level determined as the control level for a non-responder to said drug in a method according to the present invention, the drug as defined herein is administered to the subject. Preferably the invention encompasses a method of treating ovarian cancer in a subject, comprising determining the level of antibodies against VEGF in a sample from the subject, wherein when the level of anti-VEGF antibodies in a sample from the subject is above 5.7 units/ml, a drug as defined herein is administered to the subject. Drugs used in the treatment of cancer include therapeutic antibodies, such as bevacizumab.

The invention, thus, also relates a drug for use in the treatment of cancer in a subject, wherein the drug is administered to the subject when the level anti-VEGF antibodies in a sample from the subject is above a level determined as the control level for a non-responder to said drug in a method according to the present invention is determined. The skilled person will acknowledge that the embodiments of the method for predicting whether a subject to be treated for cancer with a drug will respond to said treatment as outlined herein, also apply to the drug for use in the treatment. He will acknowledge that the drug is for use in the treatment of cancer in a subject, wherein the subject is predicted to respond to the treatment, i.e. if the VEGF levels determined in a method according to the present invention are indicative for the response of the subject to the treatment. In a preferred embodiment the drug is for use in the treatment of an VEGF or VEGFR associated cancer, preferably selected from the group consisting of ovarian cancer, colorectal cancer, colon cancer, lung cancer, breast cancer, glioblastoma, kidney (renal) renal, pancreatic cancer, prostate cancer, gastric cancer, and liver cancer. The drug is preferably bevacizumamb. The invention, thus, also relates to Bevacizumab for use in the treatment of ovarian cancer in a subject, wherein bevacizumab is administered to the subject when the level anti-VEGF antibodies in a sample from the subject is above 5 units/ml, preferably above 7, more preferably above 7.5, further preferred above 8.

The invention furthermore relates to a (diagnostic) kit for diagnosing cancer, or predicting the response of a cancer patient to the treatment of an angiogenesis inhibitor, said kit comprising VEGF or an antigenic peptide thereof, and means to detect antibodies binding to said VEGF or peptide thereof. Preferably the kit is designed for a method of the present invention. It will be understood that the embodiments disclosed herein above for VEGF or an antigenic peptide thereof as set out herein above also apply to the kit. The kit is designed to detect autoimmune antibodies in samples of subject and hence comprises means to detect such antibodies, particularly antibodies binding to said VEGF or peptide thereof. Such means are outlined herein above, e.g. for immunoassays. The embodiments set out for this immunoassays apply also to the kit of the invention. The kit may further comprise standard solutions comprising VEGF antibodies in different dilutions for a standard curve of units/ml, preferably the standard solutions comprises dilutions having a concentration of VEGF antibodies as set out herein as preferred embodiments.

It will be readily understood that the embodiments outlined above shall apply to the invention as a whole and not be limited to a specific method, unless stated otherwise. It will for example be understood the embodiments for the type of cancer shall be applied to every method, kit or the like disclosed herein. The invention is further illustrated by the following non-limiting examples and figures.

```
                        Sequences
                        SEQ ID NO: 1:

Amino acid sequence of the human VEGF-A (isoform 165)
[SEQ ID NO: 1]
    1    MNFLLSWVHW  SLALLLYLHH  AKWSQAAPMA  EGGGQNHHEV  VKFMDVYQRS
   51    YCHPIETLVD  IFQEYPDEIE  YIFKPSCVPL  MRCGGCCNDE  GLECVPTEES
  101    NITMQIMRIK  PHQGQHIGEM  SFLQHNKCEC  RPNKDRARQE  NTCGPCSERR
  151    KHLFVQDPQT  CKCSCKNTDS  RCKARQLELN  ERTCRCDKPR  R
```

EXAMPLES

Example 1

We measured the anti-VEGF autoantibody in serum samples using a sandwich ELISA kit (CellTrend GmbH Luckenwalde, Germany). The microtiter 96-well polystyrene plates were coated with a polypeptide consisting of amino acids 27 to 191 of human VEGF165 of SEQ ID NO:1, derived from cell line SF21. To maintain the conformational epitopes of the protein, 1 mM calcium chloride was added to every buffer. Duplicate samples of a 1:100 serum dilution were incubated at 4° C. for 2 hours. After washing steps, plates were incubated for 60 minutes with a 1:20.000 dilution of horseradish-peroxidase-labeled goat anti-human IgG (Jackson, USA) used for detection. In order to obtain a standard curve, plates were incubated with test sera from an anti-VEGF autoantibody positive index patient. The ELISA was validated according to the FDA's "Guidance for industry: Bioanalytical method validation".

Figure 7:
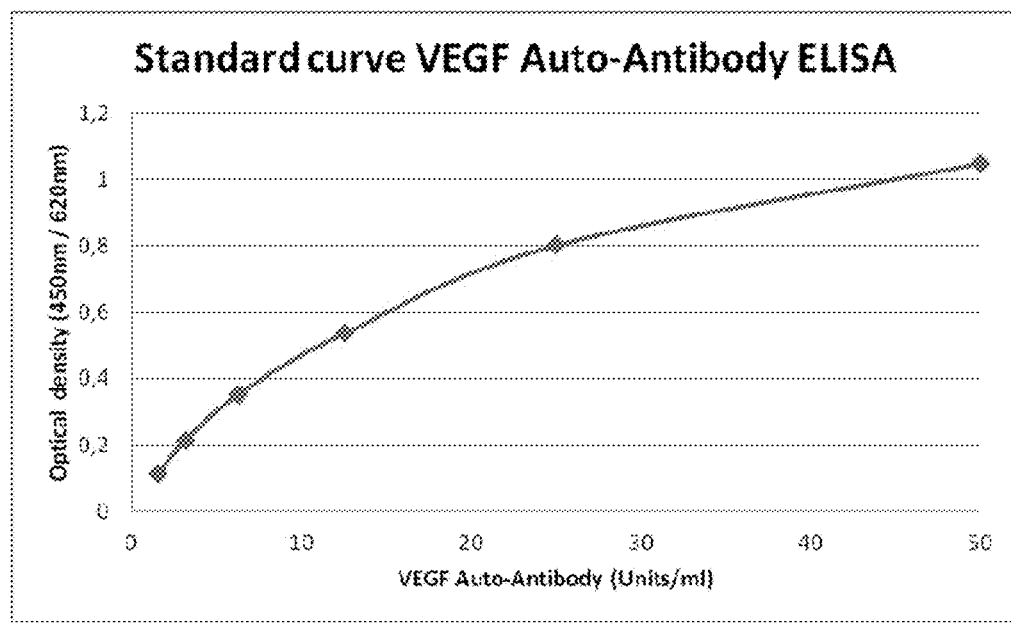
FIG. 7: Standard curve of the VEGF-Auto-Antibody ELISA

VEGF-Auto-Antibodies are not available, a serum sample from a patient with a systemic sclerosis is used for the standard curve. A 1:400 dilution of the serum sample is defined as 50 units/ml VEGF-Antibodies. A 1:100 dilution of a second systemic sclerosis patient served as a positive control (range 20.0-30.0 Units/ml). To set a standard for the concentrations of the autoimmune antibodies, a standard curve was generated. n detail, a serum sample of systemic sclerosis serum sample was diluted (a) 1:400 for standard point 50 Units/ml, (b) 1:800 for standard point 25 Units/ml, (c) 1:1600 for standard point 12.5 Units/ml, (d) 1:3200 for standard point 6.25 Units/ml, (e) 1:6400 for standard point 3.13 Units/ml and (f) 1:12800 for standard point 1.56 Units/ml. Then the optical density was determined using the kit and method of example 1. Each standard point was performed in duplicates. Results are shown in FIG. 7.

Example 2

Anti-VEGF antibody levels in serum samples from 132 healthy donors ("Control") and 201 patients with ovarian cancer ("OvCA") were measured using the kit and method of example 1. The levels were determined in units/mL. FIG. 1 shows the mean values of the natural logarithm of the VEGF antibody level for OvCA and Control subjects. Patient suffering from ovarian cancer had significantly lower levels (p≤0.0001) of anti-VEGF antibodies as compared to healthy controls.

Example 3

Figure 2:
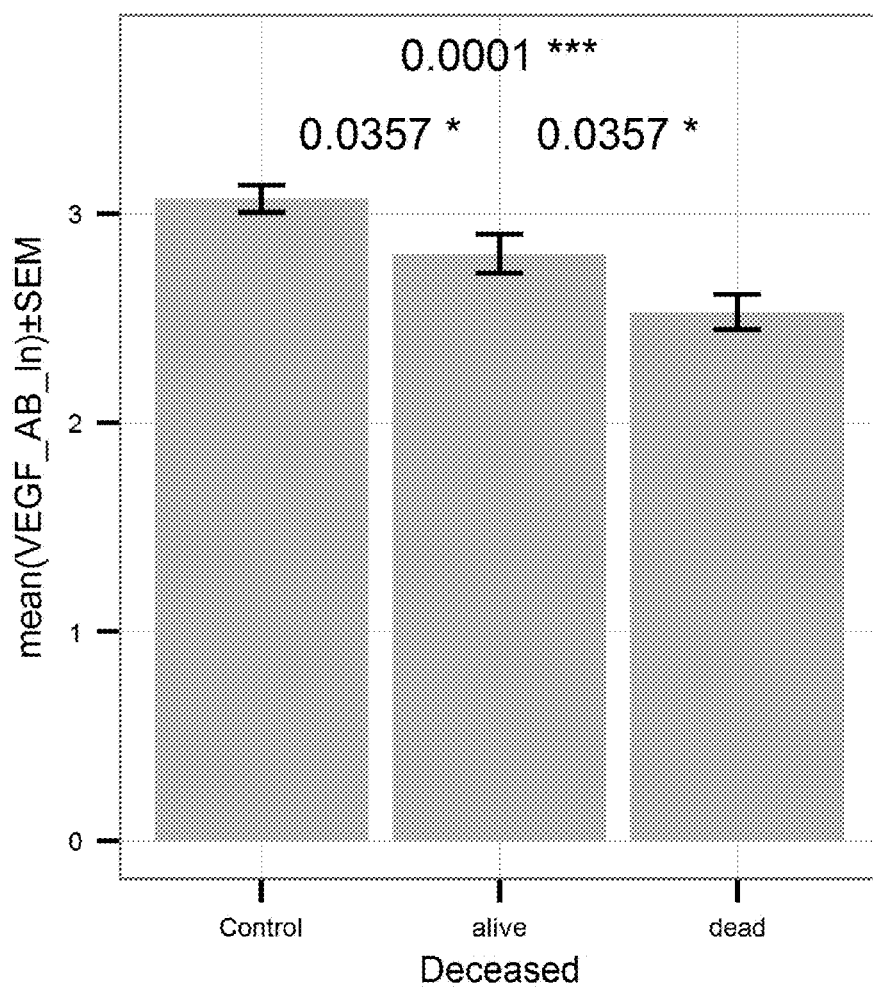
FIG. 2: Comparison of the mean level of anti-VEGF antibodies (ln of units/ml) in serum samples of ovarian cancer patients who survived ovarian cancer after surgical treatment and chemotherapy with a platinum analogue ("alive"; ln of mean=2.808; n=71) to the mean level of anti-VEGF antibodies in serum samples of ovarian cancer patients who died because of their ovarian cancer after surgical treatment and chemotherapy with a platinum analogue ("dead"; ln of mean=2.531 units/ml; n=129). The left column gives the healthy control group. P-values are indicated above (0.0357 between "control" and "alive", 0.0001 between "control" and "dead", and 0.0357 between "alive" and "dead"). Bars indicate standard error of mean.

Levels of anti-VEGF antibodies were determined in samples from patients suffering from ovarian cancer taken before onset of surgical removal of the cancer. The patients were treated with a platinum analogue after surgical removal of ovarian cancer. Results are shown in FIG. 2. Anti-VEGF antibody levels in samples of patients who survived after the treatment of the cancer were significantly higher than in those who died after said treatment.

Figure 3:
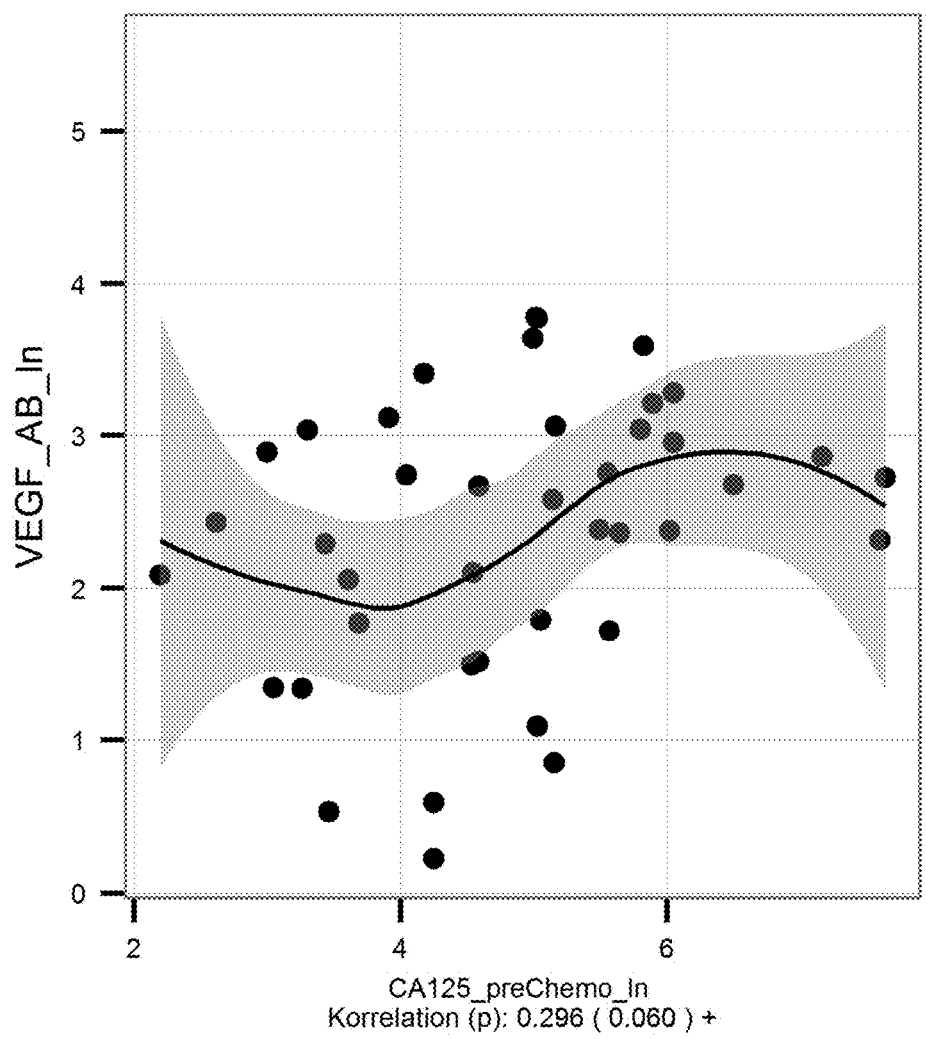
FIG. 3: (A) Correlation of mean levels of anti-VEGF antibodies (ln of units/ml) and CA 125 level [units/ml, determined with commercially availably CA 125 detection kit] in serum samples of ovarian cancer patients before onset of chemotherapy.
Figure 4:
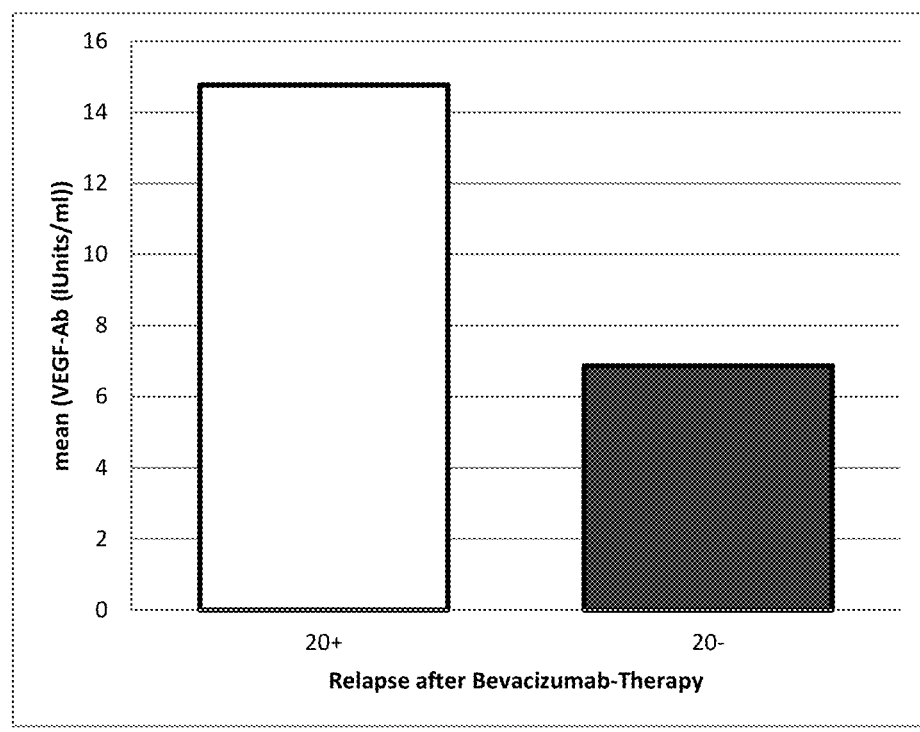
FIG. 4: anti-VEGF antibody levels in patients showing relapse or progression of ovarian cancer after treatment with bevacizumab (Avastin). Patients were categorized into patients showing relapse ("20-") or no relapse ("20+") within 20 months from onset of treatment. Mean levels were 14.77 units/ml for "20+"-group; 6.87 units/ml for the "20-"-group.

Furthermore, the levels of CA125, an approved marker for ovarian cancer, in the samples were determined and correlated with the anti-VEGF antibody levels. The results are shown in FIG. 3. A significant positive correlation could be observed between CA125 levels an levels of anti-VEGF antibodies (FIG. 3): correlation: 0.296 (p=0.060).

Example 4

Levels of the anti-VEGF-antibody were compared in patients showing relapse of ovarian cancer after therapy with bevacizumab (Avastin®) and patients showing no relapse. Treatment was conducted and monitored by physicians. Samples of patients were taken before treatment. Patients were categorized as "yes" for relapse and "no" for no relapse according to the reoccurrence of cancer after a period of 20 months.

Example 5

Figure 5:
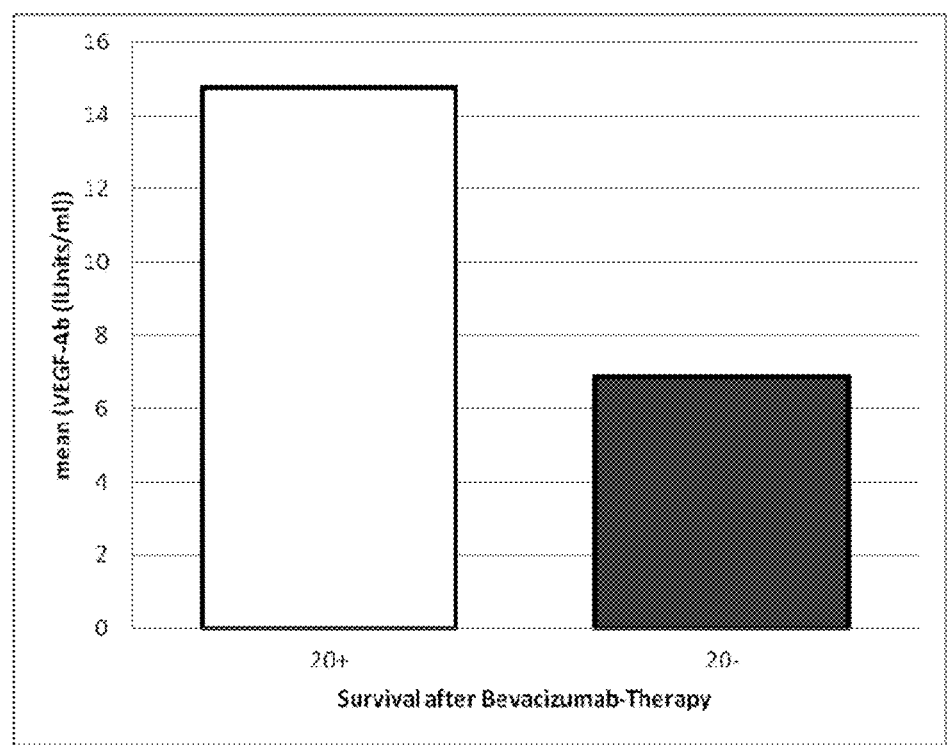
FIG. 5: anti-VEGF antibody levels in patients who died of ovarian cancer after treatment with bevacizumab (Avastin). Patients were categorized into patients not surviving ("20-") and surviving ("20+") after treatment of ovarian cancer with bevacizumamb. Mean levels were 14.77 units/ml for "20+" and 6.87 units/ml for the "20-"-group.

Serum samples of ovarian cancer patients were taken before treatment with bevacizumab. The treatment was conducted by physicians. The patients were categorized into survivors ("alive") and patients who died after treatment with bevacizumab ("dead"). The levels of anti-VEGF antibodies were determined as outlined in Example 1. The results are shown in FIG. 5. Levels of anti-VEGF antibodies were lower in patients of the "dead" group (mean: 6.87 units/rip compared to the "survival" group (mean: 14.77 units/rip, the different was significant (p=0.0014).

Example 6

The sensitivity and specificity for levels of anti-VEGF antibodies as predictor of relapse and/or mortality was calculated using ROC-analyze. Mortality and relapse were determined after treatment by surgery and platinum analogue.

The results for the prediction of relapse are given in FIG. 6A for the prediction of mortality in FIG. 6B, and for the combined endpoint prediction (relapse or death) in FIG. 6C. The results show that the levels of anti-VEGF antibodies are a good predictor for relapse or mortality after treatment of cancer patients as endpoint prediction. The specificity and sensitivity of the prediction could be further enhanced when including further factors in a multivariate model. These factors were age, Figo and histology staging.

The p-value for mortality or the combined end-point (mortality or relapse) was p<0.001 and p<0.024, respectively in the Cox-proportional hazard. For relapse as the single endpoint we observed a significant value. The p-value was 0.07.

SUMMARY

The results of the present Examples show that anti-VEGF antibody levels are significant lower in patients with ovarian cancer compared to healthy controls. Furthermore, the levels are significantly higher in patients in which show no relapse after treatment with Bevacizumab as compared to patients showing relapse or progression of cancer or who died after treatment. Levels of anti-VEGF antibodies in samples are a well suited predictor for the response to the treatment with an angiogenesis inhibitor. Relapse of cancer or mortality of the patient as endpoints of the treatment can be predicted with a high degree of specificity and sensitivity.

The invention claimed is:

1. A method for predicting whether a subject to be treated for ovarian cancer with a drug will respond to said treatment, wherein the drug is a VEGF inhibitor selected from the group consisting of bevacizumab and Aflibercept, or wherein the drug is a platinum analogue, the method comprising
(i) determining a level of antibodies against vascular endothelial growth factor (VEGF) (anti-VEGF antibodies) in a sample from said subject to be treated, wherein the anti-VEGF antibodies bind to VEGF-A of SEQ ID NO:1;
(ii) comparing the determined level of anti-VEGF antibodies in the sample to either one or both of a first and second VEGF antibody control level,
a) wherein the first VEGF antibody control level is determined from subjects not showing relapse or progression of ovarian cancer or mortality within 20 months after onset of treatment with said drug, and
b) wherein the second VEGF antibody control level is determined from subjects showing relapse or progression of ovarian cancer or mortality within 20 months after onset of treatment with said drug,
wherein a decreased level of anti-VEGF antibodies in the sample from the subject to be treated as compared to the first VEGF antibody control level and/or an equal level as compared to the second VEGF antibody control level is indicative for relapse or progression of ovarian cancer or mortality in the subject within 20 months after onset of treatment with said drug, and wherein an increased level of anti-VEGF antibodies in the sample from the subject to be treated as compared to the second VEGF antibody control level and/or an equal level as compared to the first VEGF antibody control level is indicative for no relapse and no progression of ovarian cancer and no mortality in the subject within 20 months after onset of treatment with said drug.

2. The method according to claim 1, wherein the natural logarithm of a level of antibodies against VEGF in the sample from the subject to be treated of less than 0.9 fold as compared to the natural logarithm of the mean of the first VEGF antibody control level is indicative for relapse or progression of ovarian cancer or mortality in the subject within 20 months after onset of treatment with said drug, and/or the natural logarithm of a level of antibodies against VEGF in the sample from the subject to be treated of more than 1.5 fold as compared to the natural logarithm of the mean of the second VEGF antibody control level is indicative for no relapse and no progression of ovarian cancer and no mortality in the subject within 20 months after onset of treatment with said drug.

3. The method according to claim 1, wherein the drug is bevacizumab, cisplatin or carboplatin.

* * * * *

```
SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens
<220> FEATURE:
<221> NAME/KEY: MISC_FEATURE
<222> LOCATION: (1)..(191)
<223> OTHER INFORMATION: Amino acid sequence of the human VEGF-A
      (isoform 165)

<400> SEQUENCE: 1

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190
```